United States Patent
Elson et al.

(10) Patent No.: US 7,456,267 B2
(45) Date of Patent: Nov. 25, 2008

(54) N-ACYLATED CHITINOUS POLYMERS AND METHODS OF USE THEREOF

(75) Inventors: Clive Elson, Halifax (CA); Agis Kydonieus, Kendell Park, NJ (US); Susan Elizabeth Henderson, Wellington (CA)

(73) Assignee: Kytogenics Pharmaceuticals, Inc., Chatham, NJ (US)

( * ) Notice: Subject to any disclaimer, the term of this patent is extended or adjusted under 35 U.S.C. 154(b) by 0 days.

(21) Appl. No.: 10/810,742

(22) Filed: Mar. 25, 2004

(65) Prior Publication Data

US 2005/0214255 A1 Sep. 29, 2005

(51) Int. Cl.
*C08B 37/08* (2006.01)
*A01N 43/04* (2006.01)

(52) U.S. Cl. .......................... 536/20; 514/55
(58) Field of Classification Search ............... 536/20; 514/55

See application file for complete search history.

(56) References Cited

U.S. PATENT DOCUMENTS 5,888,988 A * 3/1999 Elson .................... 514/55

* cited by examiner

*Primary Examiner*—Shaojia Anna Jiang
*Assistant Examiner*—Everett White
(74) *Attorney, Agent, or Firm*—Edwards Angell Palmer & Dodge LLP; Ralph A. Loren

(57) ABSTRACT

The invention pertains to N-acetylated, N, O-carboxyalkyl-chitosans and methods for using the chitosans to treat disorders, such as cancer, nervous system disorders, urinary tract disorders, and reproductive tract disorders.

2 Claims, No Drawings

N-ACYLATED CHITINOUS POLYMERS AND METHODS OF USE THEREOF

BACKGROUND OF THE INVENTION

Chitin (N-acetyl glucosamine) is a naturally occurring polysaccharide and many of its derivatives have applications in the biomedical field. Chitosan is a deacetylated chitin derivative and the term includes a variety of polymers with different degrees of deacetlyation and depolymerization. Most chitosans are soluble at pHs below 7 and many form hydrogels when dissolved in aqueous solutions. Chitosan has been used for a variety of applications as a biomaterial for tissue engineering, wound healing, and as an excipient for drug delivery. Chitosan can be used as a drug delivery agent for a wide variety of therapeutics. For example, DNA complexation with chitosan yields suitable nano- and micro-particulate formulations for transfection in vivo and in vitro. However, both chitin and chitosan are limited in their uses due to a lack of biocompatibility.

N,O-carboxymethylchitosan (NOCC) has been generally found to be more biocompatible than the highly deacetylated and high molecular weight chitosans. The difference has been attributed to the presence of carboxymethyl groups (—$CH_2$—$COO^-$) along the polysaccharide chain. Unfortunately, NOCC precipitates in acidic solutions. The insolubility of NOCC is undesirable for therapeutic applications in acidic environments. There is a need for polymers with good biocompatibility and solubility in acidic, basic, and neutral environments.

Accordingly, it is an object of the invention to provide novel N-acylated chitinous polymers.

It is a further object of the invention to provide polymers with expanded solubility ranges, especially at low pH's.

It is also an object of the invention to provide polymers which have moieties capable of forming covalent or ionic bonds with agents.

It is also an object of the invention to provide a method for administering an agent to a subject using an N-acylated-N,O-carboxyalkylchitosan. The agent is linked either covalently, ionically, electrostatically, or dispersed in a mixture of the polymer, which allows the agent to be released in the subject.

It is another object of the invention to provide a method for treating a subject suffering from a disorder by administering an effective amount of an N-acylated-N,O-carboxyalkylchitosan associated with a therapeutic agent.

It is further an object of the invention to provide novel cross linked N-acylated-N,O-carboxyalkylchitosan.

These and other objects, features, and advantages of the invention will be apparent from the following description and claims.

SUMMARY OF THE INVENTION

The present invention provides novel N-acylated chitinous polymers. The chitinous polymers of the invention are comprised of subunits of the formula:

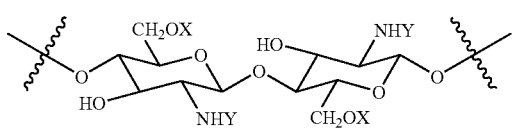

wherein

X is independently selected from hydrogen, —$(CH_2)_b$COG, or —$(CH_2)_b$COOZ for each occurrence, provided that at least 10% of X groups on said polymer are —$(CH_2)_b$COOZ or —$(CH_2)_b$COG;

Y is independently selected from —C(=O)—R—$CO_2$Z, —C(=O)—R—COG, hydrogen, carboxyalkyl, acetyl, or a pharmaceutically acceptable salt thereof for each occurrence, provided that at least 1% of Y groups on said polymer are —C(=O)—R—$CO_2$Z or —C(=O)—R—COG;

R is independently selected from the group consisting of alkyl, alkenyl, and aryl;

b is 1-8;

G is an agent or a pharmaceutically acceptable salt thereof; and

Z is hydrogen, a cation, an agent, or a pharmaceutically acceptable salt thereof.

The invention also provides methods for administering an agent to a subject. An N-acylated-N,O-carboxyalkylchitosan associated with the agent (e.g., dissolved or dispersed in a solution of the polymer, or linked, e.g., covalently, ionically or electrostatically) is administered and the agent is released in the subject.

In addition, the invention also provides a method for treating a subject suffering from a disorder by administering an effective amount of an N-acylated-N,O-carboxyalkylchitosan associated with a therapeutic agent. Particular disorders include urinary tract disorders, reproductive tract disorders, cancer, and nervous system disorders. The N-acylated-N,O-carboxyalkylchitosans may also be used to prevent surgical adhesion.

The invention also includes cross linked N-acylated-N,O-carboxyalkylchitosan and pharmaceutical compositions comprising it.

DETAILED DESCRIPTION OF THE INVENTION

The invention is directed, at least in part, to novel N-acylated chitinous polymers. The N-acylated chitinous polymers of the invention have enhanced biocompatibility properties and/or solubility. The polymers may be used for the delivery of therapeutic agents to a subject.

NOCC (N,O-carboxymethylchitosan) reacts in water solutions with the anhydrides of dicarboxylic acids, such as succinic, citraconic and glutaric acids, to form N-acylated chitinous polymers yielding a terminal carboxylate group. This increases the number of carboxylate groups per sugar, while decreasing the free amine content. An example of a subunit of N,O-carboxymethyl-N-succinyl chitosan is shown below:

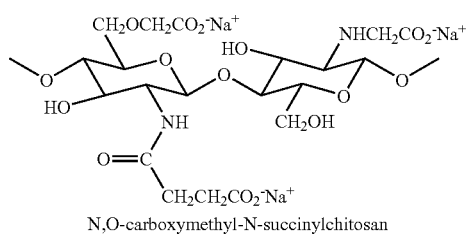

N,O-carboxymethyl-N-succinylchitosan

In the case of N,O-carboxymethyl-N-succinyl chitosan (NS—NOCC), the observed degree of carboxylation was increased by approximately 30% from 0.95 to 1.25 carboxylate groups per sugar monomer. In addition, NS—NOCC is soluble at pH's between 1 and 11, while NOCC is soluble only at pH's above 6.

The N-acylated chitinous polymers of the invention can be prepared starting with, for example, chitosan or NOCC. If chitosan is used as the starting material, the unsubstituted amine centers will react with dicarboxylic acid anhydrides, such as succinic acid, to form acylated chitosans (e.g., N-succinylchitosan). If the acylated chitosan is reacted further with chloroacetic acid, then carboxymethylation will occur at oxygen centers and at any remaining unsubstituted amine centers. This combination of reactions yields N,O-carboxymethyl-N-succinylchitosan. However, the resulting polymer has a higher degree of N-succinyl groups and fewer carboxymethyl groups on the nitrogen centers than the NS—NOCC prepared from NOCC starting material. The succinylation of chitosan may be performed either heterogeneously or homogeneously.

The invention includes chitinous polymers comprised of subunits of the formula:

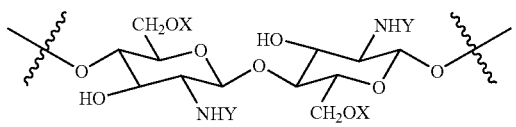

wherein

X is independently selected from hydrogen, —$(CH_2)_b$COG, or —$(CH_2)_b$COOZ for each occurrence, provided that at least 10% of X groups on said polymer are —$(CH_2)_b$COOZ or —$(CH_2)_b$COG;

Y is independently selected from —C(=O)—R—$CO_2$Z, —C(=O)—R—COG, hydrogen, carboxyalkyl, acetyl, or a pharmaceutically acceptable salt thereof for each occurrence, provided that at least 1% of Y groups on said polymer are —C(=O)—R—$CO_2$Z or —C(=O)—R—COG;

R is independently selected from the group consisting of alkyl, alkenyl, and aryl;

b is 1-8;

G is an agent or a pharmaceutically acceptable salt thereof; and

Z is hydrogen, a cation, an agent, or a pharmaceutically acceptable salt thereof.

The N-acylated chitinous polymers of the invention have at least 5%, but possibly 15%, 20%, 25%, 30%, 40%, 50%, 60%, or 70% of the X groups of the polymer are of the formula —$(CH_2)_b$COOZ or —$(CH_2)_b$COG. Advantageously, b may be 1, 2, 3, 4, or 5.

In addition, the N-acylated chitinous polymers have at least 1%, but possibly 2.5%, 5%, 7.5%, 10%, 12.5%, 15%, 17.5%, 20%, 25%, 30%, 35% or 40% of the Y groups on the polymer are —C(=O)—R—$CO_2$Z or —C(=O)—R—COG. R has the formula —$(CH_2)_a$—, wherein a is between 1-8. Advantageously, a may be 2, 3 or 4. R can also be aryl (e.g., phenyl, naphthyl, heteroaryl, etc.), alkyl or alkenyl. R may also comprise one or more heteroatoms replacing one or more carbons of the alkyl or alkenyl group.

Examples of polymers of the invention include N,O-carboxymethyl-N-succinylchitosan, N,O-carboxymethyl-N-citraconylchitosan, N,O-carboxymethyl-N-glutarylchitosan, and mixtures thereof.

Examples of cations include sodium, pottasium, calcium, magnesium, etc.

The N-acylated chitinous polymers of the invention may be water soluble at acidic, neutral, and/or basic pH's. Advantageously, the polymers may be water soluble at pH's ranging from about 1 to about 11.

The N-acylated chitinous polymers of the invention include compounds wherein Z or G is an agent. Agents include compositions, compounds, and other entities which may be attached to the N-acylated chitinous polymer. Examples of agents include therapeutic agents, dyes, labels, penetration enhancers, etc.

The agent may be associated with the polymer through a covalent, ionic, or electrostatic linkage, or it may be dissolved or dispersed in a solution containing the polymer. The agent may be covalently bonded to the polymer itself or it may be linked to the polymer through the use of an linking moiety or through an ionic or electrostatic linkage. The linking moiety may be any moiety which links the polymer to the agent. The linking moiety may be selected such that the agent is released in the subject at a desired location. Examples of linking moieties include peptides, enzymatically cleavable bonds, diazo linkages, disulfide linkages, etc. In other embodiments, the linking moiety is selected such that the agent may perform its intended function while remaining associated with the polymer.

The agent may be associated with the polymer or the linking moiety in such a manner that it is released from the polymer by a change in the pH or other environmental condition or over a period of time at a given pH. Examples of environments where a therapeutic agent can be released include the subject's intestine, stomach, urinary tract (e.g., bladder, urethra, etc.), or reproductive tract (e.g., vagina, uterus, etc.).

Examples of subjects include mammals, such as dogs, pigs, sheep, cows, cats, horses, goats, ferrets, mice, rats, rabbits, bears, monkeys, gorillas, chimpanzees, and, preferably, humans.

The term "therapeutic agent" includes drugs, peptides, oligonucleotides, and macromolecules such as proteins, polysaccharides, and nucleic acids. Examples of therapeutic agents include anti-cancer agents, agents for the treatment of nervous system disorders, anti-inflammatory agents, antibiotics, etc. Examples of agents include 5-aminosalicylic acid, doxorubicin, peptides, and mixtures thereof.

The term "drugs" includes organic compounds, with a molecular weight of between about 50 and about 1000 daltons. More preferably, the compounds have a molecular weight between about 100 daltons and about 700 daltons.

The term "peptide" includes therapeutic agents with a molecular weight between about 1000 to about 5000 daltons. Like the proteins, the peptides may be naturally occurring, recombinant or chemically synthesized.

The term "proteins" include therapeutic agents with a molecular weight between about 5000 and about 500,000 daltons, or preferably between about 5000 and about 150,000 daltons. The proteins may be naturally occurring, recombinant or chemically synthesized.

The term "therapeutic macromolecule" means any macromolecule that provides a therapeutic effect, includes mucopolysaccharides or glycosaminoglycans such as heparin.

Examples of peptides and proteins include, for example, cytokines, peptide hormones, growth factors, cardiovascular system factors, cell adhesion factors, central and peripheral nervous system factors, humoral factors, bone and skeleton factors, gastrointestinal system factors, kidney and urinary organ factors, connective tissue and skin factors, sense organs factors, immune system factors, respiratory system factors, genital organ factors, enzymes, and fragments and portions thereof.

The cytokines include lymphokines (e.g., interferons (e.g., interferon-α, -β and -γ), interleukins (e.g. interleukin 2 through 11), monokines (e.g., interleukin-1)), tumor necrosis factors (e.g. TNF-α and -β), malignant leukocyte inhibitory factor (LIF), and hematopoietic factors (e.g., erythropoietin), granulocyte colony stimulating factor (G-CSF), granulocyte-macrophage stimulating factor (GM-CSF), macrophage colony stimulating factor (M-CSF), and fragments and analogs thereof.

Examples of bone and skeleton factors include bone GLa peptide, parathyroid hormone and its active fragments (osteostatin, *Endocrinology* 129:324, 1991), histone H4-related bone formation and proliferation peptide (OGP, EMBO 11:1867, 1992), and fragments and analogs thereof.

Examples of growth factors include nerve growth factors (NGF, NGF-2/NT-3), epidermal growth factor (EGF), fibroblast growth factor (FGF), insulin-like growth factor (IGF), transforming growth factor (TGF), platelet-derived cell growth factor (PDGF), hepatocyte growth factor (HGF), and fragments and analogs thereof.

Examples of peptide hormones include insulin, growth hormone, luteinizing hormone-releasing hormone (LHRH), adrenocorticotropic hormone (ACTH), amylin, oxytocin, luteinizing hormone and other factors acting on the genital organs, and fragments and analogs thereof.

Examples of cardiovascular system factors include factors which modulate blood pressure, arteriosclerosis, and like conditions. These factors include endothelins, endothelin inhibitors, endothelin antagonists, endothelin producing enzyme inhibitors, vasopressin, renin, angiotensin I, angiotensin II, angiotensin III, angiotensin I inhibitor, angiotensin II receptor antagonist, atrial naturiuretic peptide (ANP), anti-arrythmic peptide, and fragments and analogs thereof.

Examples of central and peripheral nervous system factors include opioid peptides (e.g., enkephalins, endorphins, kyotorphins), neurotropic factor (NTF), calcitonin gene-related peptide (CGRP), thyroid hormone releasing hormone (TRH), neurotensin, and fragments and analogs thereof.

Examples of gastrointestinal system factors are secretin and gastrin. Examples of humoral factors include calcitonin, apoprotein E and hirudin and other factors which modulate hemagglutination, plasma cholesterol level or metal ion concentrations. Examples of the cell adhesion factors include laminin and intercellular adhesion molecule 1 (ICAM 1). Examples of kidney and urinary tract factors include naturiuretic peptide (BNP), urotensin, and fragments and analogs thereof. Examples of immune system factors include chemotactic peptides and bradykinins.

The term "alkyl," as used herein, includes saturated aliphatic groups, including straight-chain alkyl groups (e.g., methyl, ethyl, propyl, butyl, pentyl, hexyl, heptyl, octyl, nonyl, decyl), branched-chain alkyl groups (e.g., isopropyl, tert-butyl, isobutyl, etc.), and cycloalkyl (alicyclic) groups (e.g., cyclopropyl, cyclopentyl, cyclohexyl, cycloheptyl, cyclooctyl). The term alkyl further includes molecules having oxygen, nitrogen, sulfur or phosphorous atoms replacing one or more carbons of the hydrocarbon backbone. Preferably, a straight chain or branched chain alkyl with 10 or fewer carbon atoms in its backbone (e.g., $C_1$-$C_{10}$ for straight chain, $C_3$-$C_{10}$ for branched chain) is used, and, more preferably, 4 or fewer. Cycloalkyls may have from 3-8 carbon atoms in their ring structure, and more preferably have 5 or 6 carbons in the ring structure. The term $C_1$-$C_6$ includes alkyl groups containing 1 to 6 carbon atoms.

Moreover, the term alkyl includes both "unsubstituted alkyls" and "substituted alkyls", the latter of which refers to alkyl moieties having substituents replacing a hydrogen on one or more carbons of the hydrocarbon backbone. Such substituents can include, for example, halogen, hydroxyl, carboxylate, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), cyano, azido, nitro, or an aromatic or heteroaromatic moiety.

The term "aryl" includes groups, including 5- and 6-membered single-ring aromatic groups that may include from zero to four heteroatoms, for example, benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. The aromatic ring can be substituted at one or more ring positions with such substituents as described above, as for example, halogen, hydroxyl, alkoxy, carboxylate, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, alkylthio, nitro, cyano, or azido.

The term "alkenyl" includes unsaturated aliphatic groups analogous in length and possible substitution to the alkyls described above, but that contain at least one double bond. For example, the term "alkenyl" includes straight-chain alkenyl groups (e.g., ethylenyl, propenyl, butenyl, pentenyl, hexenyl, heptenyl, octenyl, nonenyl, decenyl), branched-chain alkenyl groups, and cycloalkenyl (alicyclic) groups (cyclopropenyl, cyclopentenyl, cyclohexenyl, cycloheptenyl, cyclooctenyl) groups. The term alkenyl further includes alkenyl groups which include oxygen, nitrogen, sulfur or phosphorous atoms replacing one or more carbons of the hydrocarbon backbone. In certain embodiments, a straight chain or branched chain alkenyl group with 10 or fewer carbon atoms in its backbone (e.g., $C_2$-$C_{10}$ for straight chain, $C_3$-$C_{10}$ for branched chain) is used. Likewise, cycloalkenyl groups may have from 3-8 carbon atoms in their ring structure, and more preferably have 5 or 6 carbons in the ring structure. The term $C_2$-$C_{10}$ includes alkenyl groups containing 2 to 10 carbon atoms.

Moreover, the term alkenyl includes both "unsubstituted alkenyls" and "substituted alkenyls", the latter of which refers to alkenyl moieties having substituents replacing a hydrogen on one or more carbons of the hydrocarbon backbone. Such substituents can include, for example, halogen, hydroxyl, carboxylate, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), cyano, azido, nitro, or an aromatic or heteroaromatic moiety.

The term "carboxyalkyl" includes carboxyl groups covalently bonded to an alkyl, alkenyl, or aryl group. The carboxyl group may be, for example, of the formula: —$(CH_2)_c COOZ$, wherein c is 1-8, and Z is as defined above. Examples of carboxyalkyl groups include carboxymethyl, carboxyethyl, carboxypropyl, and the like.

The N-acylated chitinous polymers may contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of compounds of the invention. These salts can likewise be prepared in situ during the final isolation and purification of the compounds, or by separately reacting the purified compound in its free acid form with a suitable base, such as hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

The N-acylated chitinous polymers may also contain basic functional groups, such as amino, and are, thus, capable of forming pharmaceutically acceptable salts with pharmaceutically acceptable acids. The term "pharmaceutically acceptable salts" refers to the relatively non-toxic, inorganic and organic acid addition salts of compounds of the invention. These salts can be prepared in situ during the final isolation and purification of the compounds of the invention, or by separately reacting a purified compound of the invention in its free base form with a suitable organic or inorganic acid, and isolating the salt thus formed. Representative salts include hydrobromide, hydrochloride, sulfate, bisulfate, phosphate, nitrate, acetate, valerate, oleate, palmitate, stearate, laurate, benzoate, lactate, phosphate, tosylate, citrate, maleate, funarate, succinate, tartrate, napthylate, mesylate, glucoheptonate, lactobionate, and laurylsulphonate salts and the like. (See, e.g., Berge et al. (1977) "Pharmaceutical Salts", *J. Pharm. Sci.* 66:1-19).

The invention also pertains, at least in part, to cross linked N-acylated-N,O-carboxyalkylchitosan. The N-acylated-N,O-carboxyalkylchitosans of the invention can be cross linked using agents known in the art. Examples of cross linking agents include divinyl sulfone and 1-ethyl-3-(3-dimethylaminopropyl)carbodiimide hydrochoride (EDC). In certain embodiments, a hydrogel is formed when the cross linked N-acylated-N—O-carboxyalkylchitosan is exposed to water.

The invention also includes methods for administering an agent in a subject. The invention includes administering an N-acylated-N,O-carboxyalkylchitosan associated with the agent and allowing said agent to be released in the subject. The agent may be linked covalently or ionically, or it may be dispersed within the polymer, e.g., as a polyelectrolyte dispersion.

The invention also pertains to a method for treating a subject suffering from a disorder by administering an effective amount of an N-acylated-N,O-carboxyalkylchitosan associated with a therapeutic agent. Examples of disorders which may be treated include cancer, nervous system disorders (e.g., central nervous system disorders), a urinary tract disorders, gastrointestinal tract disorders, and reproductive tract disorders.

The language "effective amount" of the polymer or agent is that amount necessary or sufficient to treat or prevent a disorder (e.g., cancer, nervous system disorders (e.g., central nervous system disorders), urinary tract disorders, gastrointestinal tract disorders, and reproductive tract disorders ) in a subject, e.g., prevent the various morphological and somatic symptoms of the particular disorder. The effective amount can vary depending on such factors as the size and weight of the subject, the type of disorder, or the particular polymer and/or agent. For example, the choice of the polymer and/or agent can affect what constitutes an "effective amount". One of ordinary skill in the art would be able to study the aforementioned factors and make the determination regarding the effective amount of without undue experimentation.

The regimen of administration can affect what constitutes an effective amount. The polymer and/or agent can be administered to the subject either prior to or after the onset of a disorder which is treatable. Further, several divided dosages, as well as staggered dosages, can be administered daily or sequentially, or the dose can be continuously infused, orally administered, or can be a bolus injection. Further, the dosages of the polymers and/or agents can be proportionally increased or decreased as indicated by the exigencies of the therapeutic or prophylactic situation.

The term "treated," "treating" or "treatment" includes therapeutic and/or prophylactic treatment. The treatment includes the diminishment or alleviation of at least one symptom associated or caused by the state, disorder or disease being treated. For example, treatment can be diminishment of one or several symptoms of a disorder or complete eradication of a disorder.

The invention also pertains to methods for treating a subject suffering from (or at risk of suffering from) a urinary tract disorder by administering an effective amount of an N-acylated-N,O-carboxyalkylchitosan associated with a therapeutic agent. Examples of urinary tract disorders include disorders of the urethra and bladder (e.g., bladder infection, e.g., interstitial cystis). Examples of therapeutic agents which can be used to treat urinary tract disorders include antibiotics and anti-inflammatory agents.

Examples of antibiotics includes chemical substances that inhibits the growth of, or kills, microorganisms. Antibiotics include, but are not limited to, penicillin, tetracyclines, clarithromycin (Biaxin®), ciprofloxacin (Cipro®), and metronidazole (Flagyl®).

Examples of anti-inflammatory agents include non-steroidal anti-inflammatory drug(s) (NSAIDs), cytokine suppressive anti-inflammatory drug(s) (CSAIDs), MK-966 (COX-2 Inhibitor), iloprost, methotrexate, thalidomide and thalidomide-related drugs (e.g., Celgen), leflunomide, tranexamic acid, T-614, prostaglandin E1, tenidap, naproxen, meloxicam, ibuprofen, piroxicam, diclofenac, indomethacin, sulfasalazine, azathioprine, ICE inhibitors (inhibitors of the enzyme interleukin-1β converting enzyme), zap-70 and/or lck inhibitors (inhibitor of the tyrosine kinase zap-70 or lck), corticosteroid anti-inflammatory drugs (e.g., SB203580), TNF-convertase inhibitors, interleukin-17 inhibitors, gold, penicillamine, chloroquine, hydroxychloroquine, chlorambucil, cyclophosphamide, cyclosporine, total lymphoid irradiation, anti-thymocyte globulin, CD5-toxins, lobenzarit disodium, cytokine regulating agents (CRAs) HP228 and HP466, prednisone, orgotein, glycosaminoglycan polysulphate, minocycline, anti-IL2R antibodies, auranofin, phenylbutazone, meclofenamic acid, flufenamic acid, intravenous immune globulin, zileuton, mycophenolic acid (RS-61443), tacrolimus (FK-506), sirolimus (rapamycin), amiprilose (therafectin), cladribine (2-chlorodeoxyadenosine), azaribine, and methotrexate.

The invention also includes methods for treating or preventing a reproductive tract disorder in a subject by administering an effective amount of an N-acylated-N,O-carboxyalkylchitosan associated with a therapeutic agent, to treat the reproductive tract disorder. The reproductive tract disorder may be a disorder of the female reproductive tract (e.g., vagina, uterus, etc.). Examples of such disorders include cancers, infections, infertility, uterine fibroids, pelvic masses, and endometriosis. The therapeutic agent may be, for example, an antibiotic or an anti-inflammatory agent.

The invention also pertains to a method of preventing surgical adhesion by using an effective amount of an N-acylated-N,O-carboxyalkylchitosan of the invention.

The invention also pertains to methods of treating a subject suffering from cancer administering an effective amount of an N-acylated-N,O-carboxyalkylchitosan associated with an anti-cancer agent. Examples of treatable cancers include cancers of the digestive tract (e.g., cancers of the mouth, stomach, intestine, and/or colon); reproductive tract (e.g., cancers of the uterus, cervix, etc.), skin, and bladder.

Examples of anti-cancer agents include agents which are known in the art (see e.g., Gilman A. G., et al., *The Pharmacological Basis of Therapeutics,* 8th Ed., Sec 12:1202-1263 (1990)), and are typically used to treat cancers. Examples of anti-cancer agents include bleomycin, docetaxel (Taxotere), doxorubicin, edatrexate, etoposide, finasteride (Proscar), flutamide (Eulexin), gemcitabine (Gemzar), goserelin acetate (Zoladex), granisetron (Kytril), irinotecan (Campto/Camptosar), ondansetron (Zofran), paclitaxel (Taxol), pegaspargase (Oncaspar), pilocarpine hydrochloride (Salagen), porfimer sodium (Photofrin), interleukin-2 (Proleukin), rituximab (Rituxan), topotecan (Hycamtin), trastuzumab (Herceptin), tretinoin (Retin-A), triapine, vincristine, vinorelbine tartrate (Navelbine), adrenocorticosteroids (e.g., prednisone), progestins (hydroxyprogesterone caproate, medroxyprogesterone acetate, megestrol acetate, etc.), estrogens (e.g., diethylstilbestrol, ethenyl estradiol, etc.), antiestrogens (e.g. tamoxifen, etc.), androgens (e.g., testosterone propionate, fluoxymesterone, etc.), antiandrogens (e.g., flutamide); and gonadotropin-releasing hormone analogs (e.g., leuprolide). Other examples of anti-cancer agents include alkylating drugs such as nitrogen mustards (e.g., mechlorethamine ($HN_2$), cyclophosphamide, ifosfamide, melphalan (L-sarcolysin), chlorambucil, etc.), ethylenimines, methylmelamines (e.g., hexamethylmelamine, thiotepa, etc.), alkyl sulfonates (e.g., busulfan, etc.), nitrosoureas (e.g., carmustine (BCNU), lomustine (CCNU), semustine (methyl-CCNU), streptozocin (streptozotocin), etc.), triazenes (e.g., decarbazine (DTIC; dimethyltriazenoimi-dazolecarboxamide)), alkylators (e.g., cis-diamminedichloroplatinum II (CDDP)), etc. Other examples of anti-cancer agents include antimetabolites such as folic acid analogs (e.g., methotrexate (amethopterin)), pyrimidine analogs (e.g., fluorouracil ('5-fluorouracil; 5-FU), floxuridine (fluorode-oxyuridine), FUdr, cytarabine (cyosine arabinoside), etc.), purine analogs (e.g., mercaptopurine (6-mercaptopurine; 6-MP), thioguanine (6-thioguanine; TG); and pentostatin (2'-deoxycoformycin)), etc. Other examples of anti-cancer agents also include vinca alkaloids (e.g., vinblastin (VLB) and vincristine), topoisomerase inhibitors (e.g., etoposide, teniposide, camptothecin, topotecan, 9-amino-campotothecin CPT-11, etc.), antibiotics (e.g., dactinomycin (actinomycin D), adriamycin, daunorubicin, doxorubicin, bleomycin, plicamycin (mithramycin), mitomycin (mitomycin C), Taxol, Taxotere, etc.), enzymes (e.g., L-asparaginase), and biological response modifiers (e.g., interferon-; interleukin 2, etc.). Other chemotherapeutic agents include cis-diaminedichloroplatinum II (CDDP); carboplatin, anthracendione (e.g., mitoxantrone), hydroxyurea, procarbazine (N-methylhydrazine), and adrenocortical suppressants (e.g., mitotane, aminoglutethimide, etc.). BCG, α-interferon, valrubicin, and mytomicin may also be used to treat certain types of cancers, such as bladder cancer.

Furthermore, the N-acylated-N,O-carboxyalkylchitosans of the invention may also be used during an operation to remove a tumor or other undesired growth, optionally in combination with one or more cancer drugs, to prevent surgical adhesion or metastasis of the tumor.

The invention also pertains to methods for treating a subject suffering from a nervous system disorder by administering an effective amount of an N-acylated-N,O-carboxyalkylchitosan associated with a therapeutic agent, to treat the nervous system disorder. Examples of nervous system disorders include anxiety, psychosis, depression, epilepsies, mania, drug addictions, and opioid and analgesic dependencies. Examples of other nervous system disorders which may be treated using the methods of the invention include neurodegenerative disorders, e.g., central nervous system degenerative disorders, neuropathies, Alzheimer's disease, Parkinson's disease, Huntington's disease, amyotropic lateral sclerosis, motor neuron disease, and multiple sclerosis.

Examples of agents which may be used to treat nervous system disorders include local and general anaesthesics, opioids, analgesics, hypnotics, sedatives, general and local riluzole, cognex, aricept, sinmet, sinmet CR, permax, parlodel, elepryl, symmetrel, artane, gabapentin, growth factors (e.g., CNTF, BDNF, IGF-1, etc.), nitric oxide synthase inhibitors, cyclo-oxygenase inhibitors (e.g., aspirin, ICE inhibitors, etc.). Other examples of agents include neuroprotective agents, such as compounds that remove protein build up (e.g., geldanamycin), anti-inflammatory agents (e.g., glucocorticoids, non-steroidal anti-inflammatory drugs (e.g., ibuprofin, aspirin, etc.), omega-3 fatty acids (e.g., EPA, DHA, etc.), minocycline, dexanabinol, etc.), compounds that increase energy available to cells (e.g., creatine, creatine phosphate, dichloroacetate, nicotinamide, riboflavin, carnitine, etc.), anti-oxidants (e.g., pyruvate, lutein, plant extracts (e.g., gingko biloba), co-enzyme Q-10, vitamin E (alpha-tocopherol), vitamin C (ascorbic acid), vitamin A (beta-carotene), selenium, lipoic acid, selenine, etc.), anti-glutamate therapies (e.g., remacemide, riluzole, lamotrigine, gabapentin, etc.), GABA-ergic therapies (e.g., baclofen, muscimol, etc.), gene transcription regulators (e.g., glucocorticoids, retinoic acid, etc.), erythropoietin, TNF-α antagonists, cholinesterase inhibitors, N-methyl-D-aspartate (NMDA) antagonists, opioid antagonists, neuronal membrane stabilizers (e.g., CDP-choline, etc.), N-acetylcysteine, procysteine, calcium and sodium channel blockers, prednisone, etc. The therapeutic agent may also be an anti-inflammatory agent or an antibiotic.

The invention also includes pharmaceutical compositions which comprise a polymer of the invention and, optionally, an additional pharmaceutically acceptable carrier. The polymer of the invention may be crosslinked. The polymer of the invention may be used as a pharmaceutically acceptable carrier, for example, when therapeutic agents are attached to it or dispersed in it.

The language "pharmaceutical composition" includes preparations suitable for administration to mammals, e.g., humans.

The phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Formulations of the present invention include those suitable for oral, nasal, topical, transdermal, buccal, sublingual, rectal, vaginal, pulmonary and/or parenteral administration. The formulations may conveniently be presented in unit dosage form and may be prepared by any methods well known in the art of pharmacy.

Methods of preparing these formulations or compositions include the step of bringing into association a polymer of the present invention with a therapeutic agent and, optionally, one or more accessory ingredients. The therapeutic agent may be dispersed in the polymer of the invention or ionically or covalently bonded to it.

Formulations of the invention suitable for oral administration may be in the form of capsules, pills, tablets, and the like, each containing a predetermined amount of a therapeutic agent and a polymer of the present invention.

In solid dosage forms of the invention for oral administration (capsules, tablets, pills, dragees, powders, granules and the like), the therapeutic agent is mixed with (or covalently bonded to) the polymer of the invention and, optionally, mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the therapeutic agent therein using, for example, hydroxypropylmethyl cellulose in varying proportions to provide the desired release profile.

Formulations of the pharmaceutical compositions of the invention for rectal or vaginal administration may be presented as a suppository, which may be prepared by bringing into association a polymer of the invention and a therapeutic agent, and mixing the polymer, optionally, with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity.

The ointments, pastes, creams and gels may contain, in addition to the polymer of this invention, additional excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

These compositions may also contain adjuvants such as wetting agents, emulsifying agents and dispersing agents. Prevention of the action of microorganisms may be ensured by the inclusion of various antibacterial, antiparasitic and antifungal agents, for example, paraben, chlorobutanol, phenol sorbic acid, and the like. It may also be desirable to include isotonic agents, such as sugars, sodium chloride, and the like into the compositions.

The phrases "parenteral administration" and "administered parenterally" as used herein means modes of administration other than enteral and topical administration, usually by injection, and includes, without limitation, intrathecal, intracapsular, intraorbital, intradermal, intraperitoneal, transtracheal, subcutaneous, subcuticular, intraarticular, subcapsular, subarachnoid, intraspinal and intrasternal injection and infusion.

These compounds may be administered to humans and other animals for therapy by any suitable route of administration, including orally, rectally, intravaginally, parenterally, intracisternally and topically.

Actual dosage levels of the therapeutic agents in the pharmaceutical compositions of this invention may be varied so as to obtain an amount of the therapeutic agent which is effective to achieve the desired therapeutic response for a particular patient, composition, and mode of administration, without being toxic to the patient.

The selected dosage level will depend upon a variety of factors including the activity of the therapeutic agent employed, or the ester, salt or amide thereof, the route of administration, the time of administration, the rate of excretion of the particular agent being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the therapeutic agents of the invention employed in the pharmaceutical composition at levels lower than that required in order to achieve the desired therapeutic effect and gradually increase the dosage until the desired effect is achieved.

The N-acylated N, O carboxyalkyl chitosan of the invention can be made in the form of microcapsules, nanocapsules, gels, polymers or thin films. The therapeutic agents can be in the form of solutions or dispersed within the polymer.

The invention is further explained by the following examples.

EXAMPLE 1

Synthesis of
N,O-Carboxymethyl-N-Succinylchitosan
(NS—NOCC)

This example describes the synthesis of a polymer of the invention, N,O-carboxymethyl-N-succinylchitosan, from NOCC.

15 kilograms of water solution containing 150 grams of a high viscosity NOCC was stirred as 105 grams of succinic anhydride was added over 30 minutes at room temperature. The pH was maintained between 7-9. The reaction was allowed to proceed for 2.5 hours. The mixture was added to 40 liters of anhydrous isopropanol and the resulting precipitate was collected by filtration. The product was washed 3 times in 80% methanol/water and then air-dried. The yield was 186 grams.

The product was a white, totally soluble solid with a viscosity of 900 cps for a 1% solution (Brookfield, spindle #4, 20C) and having an ash of 23.4%. The degree of carboxylation was 1.3.

EXAMPLE 2

Alternate Synthesis of
N,O-Carboxymethyl-N-Succinylchitosan
(NS—NOCC)

This example describes an alternate method for the synthesis of a polymer of the invention, N,O-carboxymethyl-N-succinylchitosan, in this case from chitosan.

N-Succinylation of Chitosan 11.0 grams of high viscosity chitosan was added to 1 liter of 0.12% hydrochloric acid and stirred for 1.75 hours. The pH was adjusted to 4. 17.5 grams of solid succinic anhydride was added over 40 minutes while the pH was maintained at 5-6 by addition of dilute sodium hydroxide. The mixture was stirred for 3.5 hours. The final pH was 6.

The solution was then transferred to dialysis sacks and soaked for 4 days with frequent changes of water. The contents of the dialysis sacks were then filtered through 120 micron screening. The product was then precipitated and washed in isopropanol and then air dried. The yield of N-succinylchitosan was 6.2 grams with a degree of succinylation of 0.9 and a residue upon ignition of 9.2%.

Carboxymethylation of N-succinylchitosan

A slurry 35 grams of N-succinylchitosan in 770 milliliters of anhydrous isopropanol was prepared and 115 grams of 30% sodium hydroxide was added over 20 minutes. 41 grams of chloroacetic acid was added to the mixture over 25 minutes at room temperature. The mixture was then heated to 60° C. and the temperature was maintained for 3.3 hours. The product was collected by filtration and washed in 80% methanol/water three times. The product was collected and air dried to yield 45 g. The product was soluble in water and had a total degree of carboxylation of 1.2.

EXAMPLE 3

Heterogeneous Succinylation of Chitosan

This example describes an alternate method to succinylate chitosan.

A slurry of 33 grams of high viscosity chitosan in 3 kilograms of water was prepared and stirred. 54 grams of succinic anhydride was added over 50 minutes and the pH of the mixture was maintained between 7 and 9 by the addition of 10M sodium hydroxide. The mixture was stirred for a further 4 hours. The chitinous material was partially dissolved. The product was precipitated by adding the mixture to 7 liters of isopropanol. The voluminous product was then washed with 80% methanol/water and air dried. The yield of the product was 46 grams. The resulting product was a viscous, lubricious solution in water and insoluble in 1% acetic acid. The solutions of the product did not form firm gels after the addition of glyoxal. The degree of carboxylation was determined to be 0.7.

EXAMPLE 4

Synthesis of N,O-Carboxymethyl,
N-Citraconylchitosan (NC—NOCC)

This example describes the synthesis of a polymer of the invention, N,O-carboxymethyl-N-citraconylchitosan, from NOCC.

5 grams of low viscosity NOCC was dissolved in 250 milliliters of water and 9.35 grams of citraconic anhydride was added with stirring over 33 minutes at room temperature. The pH was maintained between 7 and 9 and the reaction was allowed to proceed for forty five minutes. The resulting mixture was placed in dialysis tubing (MWCO 12,000) and soaked for 3 days with frequent water changes. The contents of dialysis tubing were transferred to petri-dishes and freeze dried to obtain 3.3 grams of solid product. The product had an ash content of 16.9% and a degree of substitution of 1.12. The product was soluble at all pH's between 2 and 10.

EXAMPLE 5

Synthesis of
N,O-Carboxymethyl-N-Glutarylchitosan
(NG-NOCC)

This example describes the synthesis of a polymer of the invention, N,O-carboxymethyl-N-glutarylchitosan, from NOCC.

Water (0.9 kilograms) containing 3 grams of a high viscosity NOCC was stirred as 2.3 grams of glutaric anhydride was added over 20 minutes at room temperature. The pH was maintained between 7-9. The reaction was allowed to proceed for 3.5 hours. The mixture was added to 2 liters of anhydrous isopropanol and the resulting precipitate was collected by filtration. The product was washed 3 times in 80% methanol/water and then air-dried. The yield was 3.4 grams.

The product was white, almost totally soluble with a viscosity of 1100 cps for a 1% solution in water (Brookfield, spindle #4, 20C) and had an ash content of 20.8%. The degree of carboxylation was 1.02.

EXAMPLE 6

Coupling of Taurine (2-aminoethanesulfonic acid) to
N,O-carboxymethyl-N-succinylchitosan
(NS—NOCC)

This example describes the coupling of an agent, taurine, to N,O-carboxymethyl-N-succinylchitosan.

10 grams of high viscosity NS—NOCC was added to 1 liter of 0.25% saline solution. The solution was stirred to dissolve the NS—NOCC. 34.3 grams of taurine was added as solid to NS—NOCC solution. The solution stirred to dissolve the solid. The pH of the mixture was adjusted to 6 and a solution containing 35 grams of 1-ethyl-3-(3-dimethylaminopropyl) carbodiimide hydrochoride (EDC) plus 2.1 grams of N-hydroxysuccinide (NHS) also at pH 6 was added. The mixture was stirred for 1.25 hours and left overnight. The dialysis tubing was filled with the resulting mixture and soaked for 3 days with frequent changes of water. The contents of dialysis tubing were air dried to obtain 9.9 grams of light yellow colored product.

The sulfur content of the product was 6.65% which indicated a degree of coupling or degree of substitution of taurine of approximately 0.7 per sugar.

EXAMPLE 7

Coupling of 5-ASA (5-aminosalicylic acid) to N,O-Carboxymethyl-N-Succinylchitosan (NS—NOCC)

This example describes the coupling of an agent, 5-ASA, to N,O-carboxymethyl-N-succinylchitosan.

2 grams of high viscosity NS—NOCC was added to 0.5 kilograms of 0.25% saline solution. The resulting mixture was stirred until the NS—NOCC was dissolved. The pH was adjusted to 1.1 using hydrochloric acid. 7.0 grams of solid 5-ASA was added to the NS—NOCC solution and the solution was readjusted to pH to 0.9, yielding a clear solution. 3.5 grams of EDC and 0.2 grams NHS were then dissolved in 10 milliters water and the pH of the resulting solution was adjusted to 1.4. Immediately, the EDC/NHS mixture was added to the NOCC plus 5-ASA solution and stirred at a pH of 0.9 for 2 hours. The resulting solution was poured into 1.6 liters of anhydrous isopropanol to form a precipitate that was collected, washed in more isopropanol and air-dried. The product was a white powder that weighed 1.0 grams.

Comparison of the ultra-violet absorbance at 302 nm of the coupled, 5-ASA-NS—NOCC product, in 0.1M HCl solution to standard solutions of 5-ASA indicated that the degree of substitution of 5-ASA was 0.03 per sugar.

EXAMPLE 8

Coupling of Doxorubicin Hydrochloride (Adriamycin) to N,O-Carboxymethyl-N-Succinylchitosan (NS—NOCC)

This example describes the coupling of an agent, doxorubicin hydrochloride, to N,O-carboxymethyl-N-succinylchitosan.

0.38 grams of high viscosity NS—NOCC was added to 38 grams of 0.25% saline solution. The resulting solution was then stirred to dissolve the solid and the pH was adjusted to 6. EDC (0.66 grams) was added to 20 ml water and the pH of the resulting solution was adjusted to pH to 5.9. NHS (0.10 g) was then added to 20 ml water and the pH of the resulting solution was adjusted to 6. 1 ml of EDC solution was then mixed with 1 ml of NHS solution and subsequently added to the NS—NOCC solution. The pH of the resulting solution was then adjusted to 6.1. 50 mg of doxorubicin hydrochloride in 7 ml water was then added dropwise over 3 minutes to the activated NS—NOCC solution. The resulting mixture was then stirred for 2.5 hours at room temperature and left standing overnight. The product was then transferred into dialysis sacks (MWCO 12,000) and soaked for 4 days with frequent changes of water (pH 5.5). The contents of the dialysis sacks were then freeze dried to obtain 0.25 g of orange-colored product.

Comparison of the visible absorbance at 494 nm of the coupled, doxorubicin-NS—NOCC product in aqueous solution to a standard solutions of doxorubicin hydrochloride indicated that the product contained 1.1% doxorubicin by weight.

EXAMPLE 9

Formation of Hydrogel from N,O-carboxymethyl-N-succinylchitosan (NS—NOCC)

This example describes a method for synthesizing a hydrogel from N,O-carboxymethyl-N-succinylchitosan.

0.63 grams of NS—NOCC was dissolved in 25 milliliters of 0.4M sodium hydroxide. 0.47 milliliters of divinyl sulfone solution (Aldrich Chemical, 97%, density 1.177 g/ml) was then added to the solution. Within a minute, the solution became bright yellow and a firm gel formed. The gel was transferred to dialysis tubing and soaked for 4-6 days with changes of water. The gel was then removed from the tubing and dried at room temperature to yield 0.61 g of product. Re-hydration of the product in water formed a gel that bound 100 times the mass of the cross-linked product. In saline, the solid product swelled 35 times.

The foregoing examples are merely exemplary and those skilled in the art will be able to determine other modifications to the described procedures which fall within the scope of the invention. Accordingly, the invention is defined by the following claims and equivalents thereof.

What is claimed is:

1. An N-acylated chitinous polymer, wherein said chitinous polymer is comprised of subunits of the formula:

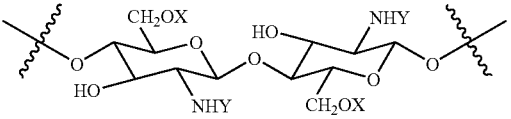

wherein

X is independently selected from hydrogen, —$(CH_2)_b$COG, or —$(CH_2)_b$COOZ for each occurrence, provided that at least 10% of X groups on said polymer are —$(CH_2)_b$COOZ or —$(CH_2)_b$COG;

Y is independently selected from —C(=O)—R—$CO_2$Z, —C(=O)—R—COG, hydrogen, carboxyalkyl, acetyl, or a pharmaceutically acceptable salt thereof for each occurrence, provided that at least 1% of Y groups on said polymer are —C(=O)—R—$CO_2$Z or —C(=O)—R—COG;

R is aryl;

b is 1-8;

G is an agent or a pharmaceutically acceptable salt thereof; and

Z is hydrogen, a cation, an agent, or a pharmaceutically acceptable salt thereof.

2. An N-acylated chitinous polymer, wherein said chitinous polymer is comprised of subunits of the formula:

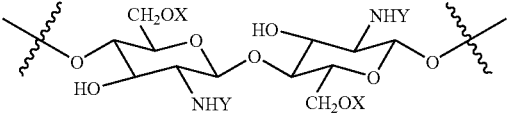

wherein

X is independently selected from hydrogen, —$(CH_2)_b$COG, or —$(CH_2)_b$COOZ for each occurrence, provided that at least 10% of X groups on said polymer are —$(CH_2)_b$COOZ or —$(CH_2)_b$COG;

Y is independently selected from —C(=O)—R—$CO_2$Z, —C(=O)—R—COG, hydrogen, carboxyalkyl, acetyl, or a pharmaceutically acceptable salt thereof for each occurrence, provided that at least 1% of Y groups on said polymer are —C(=O)—R—$CO_2$Z or —C(=O)—R—COG;

R is independently selected from the group consisting of alkyl, alkenyl, and aryl; wherein R further comprises one or more heteroatoms replacing one or more carbons of the alkyl or alkenyl group;

b is 1-8;

G is an agent or a pharmaceutically acceptable salt thereof; and

Z is hydrogen, a cation, an agent, or a pharmaceutically acceptable salt thereof.

* * * * *